United States Patent
Kubo

(10) Patent No.: US 11,849,919 B2
(45) Date of Patent: Dec. 26, 2023

(54) ENDOSCOPE AND CASE BODY

(71) Applicant: OLYMPUS CORPORATION, Tokyo (JP)

(72) Inventor: Takafumi Kubo, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 471 days.

(21) Appl. No.: 17/125,092

(22) Filed: Dec. 17, 2020

(65) Prior Publication Data
US 2021/0137361 A1 May 13, 2021

Related U.S. Application Data

(63) Continuation of application No. PCT/JP2019/007347, filed on Feb. 26, 2019.

(30) Foreign Application Priority Data

Jul. 4, 2018 (JP) .................................. 2018-127780

(51) Int. Cl.
*A61B 1/00* (2006.01)

(52) U.S. Cl.
CPC ...... *A61B 1/00121* (2013.01); *A61B 1/00042* (2022.02); *A61B 1/00066* (2013.01)

(58) Field of Classification Search
CPC .................. A61B 1/00042; A61B 1/00066
See application file for complete search history.

(56) References Cited

U.S. PATENT DOCUMENTS

| 4,294,555 A | 10/1981 | Galaske et al. |
| 4,845,555 A | 7/1989 | Yabe et al. |
| 2017/0196435 A1* | 7/2017 | Sato ................... A61B 1/00042 |
| 2022/0240755 A1* | 8/2022 | Kimura .................. H01H 13/14 |

FOREIGN PATENT DOCUMENTS

| JP | S55-123726 A | 9/1980 |
| JP | S63-197430 A | 8/1988 |
| JP | 2001-209830 A | 8/2001 |
| JP | 2009-261708 A | 11/2009 |
| JP | 2012-235814 A | 12/2012 |
| JP | 2014-023953 A | 2/2014 |

OTHER PUBLICATIONS

International Search Report dated May 14, 2019 issued in PCT/JP2019/007347.

* cited by examiner

*Primary Examiner* — Matthew J Kasztejna
(74) *Attorney, Agent, or Firm* — Scully, Scott, Murphy & Presser, P.C.

(57) ABSTRACT

An endoscope includes: a second exterior member formed by resin molding; a through hole formed in the second exterior member and having a center axis; an operating member disposed in the through hole, the operating member having a moving member configured to move along a predetermined axis; and a connecting member being fixedly mounted in the though hole, the connecting member being disposed so as to make the predetermined axis of the operating member intersect with the center axis of the though hole at a preliminarily set angle.

20 Claims, 13 Drawing Sheets

ENDOSCOPE AND CASE BODY

CROSS REFERENCE TO RELATED APPLICATION

This application is a continuation application of PCT/JP2019/007347 filed on Feb. 26, 2019 and claims benefit of Japanese Application No. 2018-127780 filed in Japan on Jul. 4, 2018, the entire contents of which are incorporated herein by this reference.

BACKGROUND OF THE INVENTION

1. Field of the Invention

The present invention relates to an endoscope which includes an exterior member made of resin and having a plurality of mounting holes for mounting electric components or mechanism components, and a case body which includes such an exterior member.

2. Description of the Related Art

In general, an endoscope for medical use includes: an insertion section inserted into a body cavity; and an operation section disposed on a proximal end side of the insertion section.

There has been known an endoscope where a bending portion which is bendable, for example, in four directions, that is, in upward, downward, leftward and rightward directions, or in two directions, that is, in upward and downward directions, is mounted on the insertion section. In such an endoscope, a bending operation device which bends the bending portion is mounted on the operation section. A user can perform a bending control of the bending portion by operating the bending operation device with fingers of a user's hand which grasp the operation section.

There has also been known an endoscope where a fluid conduit (channel) for air/water feeding or suction is formed in the insertion section. In such an endoscope, a controller for controlling air/water feeding and a controller for controlling suction are mounted on the operation section. The user can perform an air/water feeding control or a suction control by suitably operating the controllers with the fingers of the user's hand which grasp the operation section.

There has also been known an endoscope where a bending portion and a channel for fluid are formed in an insertion section, and a bending operation device and a fluid control device are mounted on an operation section.

An operation section for endoscope disclosed in Japanese Patent Application Laid-Open Publication No. 2014-23953 is formed by mounting an angle knob, an air/water feeding button, a suction button, a first push button switch, a second push button switch, a third push button switch and the like on a case. A universal cord extends from the case.

The case is an exterior member made of resin. The case includes a case body having openings, and a lid which closes the openings.

In the case body, the angle knob is disposed on a bottom plate of the case body which corresponds to a side surface of the operation section. Four components that is, the air/water feeding button, the suction button, the first push button switch, and the second push button switch are disposed on a front plate which is one of four plate portions disposed in a periphery which surrounds the bottom plate. The third push button switch is disposed on an upper plate which is one of the plate portions disposed adjacently to the front plate.

As shown in FIG. 1A, four mounting holes are formed in the front plate 101 of the case body 100. Specifically, in addition to a mounting hole 102 for air/water feeding button and a mounting hole 103 for suction button, button switch mounting holes (abbreviated as switch holes) 104, 105 for respectively mounting first and second push button switches are formed in the front plate 101. A switch hole 107 for mounting a third push button switch is formed in the upper plate 106. A shaft hole 109 through which a shaft member for disposing an angle knob is inserted is formed in a bottom plate 108. Symbol 110 indicates an opening. An insertion hole 112 for frame in which a frame is disposed in an inserting manner is formed in a lower plate 111 which is disposed adjacently to the front plate 101 and faces the upper plate 106.

Hole center axes a102, a103, a104 and a105 of four mounting holes 102, 103, 104 and 105 formed in the front plate 101 of the case body 100 are arranged parallel to each other. Accordingly, operation directions of the air/water feeding button, the suction button and two push button switches fixedly mounted in the respective mounting holes 102, 103, 104, 105 are hole center axis directions and become the same direction.

As described above, when the push button switches are disposed adjacently to each other on the front plate of the operation section for endoscope, by changing the directions of the buttons, that is, by changing the arrangement positions and the operating directions of the buttons disposed adjacently to each other in different directions from each other, an erroneous operation is prevented and hence, operability is enhanced.

For example, as shown in FIG. 1B, a case body 100A may be provided where a second push button switch mounting hole 105A for mounting a second push button switch is formed in a slanted surface 113 disposed adjacently to the upper plate 106.

However, a mold 120 for forming the above-mentioned case body 100 by resin molding includes, as shown in FIG. 1C and FIG. 1D, angular pins 121, 122, 123 and slide cores 131, 132, 133.

The first angular pin 121, in performing an open/close operation of the mold 120 in a direction of an arrow Ya, moves the first slide core 131 in a direction of an arrow Yb which differs from the open/close direction.

The second angular pin 122 moves the second slide core 132 in a direction of an arrow Yc which differs from the open/close direction. The third angular pin 123 moves the third slide core 133 in the direction of the arrow Yc which differs from the open/close direction and in a direction opposite to the moving direction of the second slide core 132.

The above-mentioned first slide core 131 includes four protruding portions 134 and the like for forming four mounting holes 102, 103, 104 and 105. The second slide core 132 includes a protruding portion 135 for forming the insertion hole 112 for frame. The third slide core 133 includes a protruding portion 136 for forming the mounting hole 107. A block 137 mounted on a movable mold which moves at the time of opening or closing the mold includes a protruding portion 138 for forming a shaft hole 109.

SUMMARY OF THE INVENTION

According to one aspect of the present invention, there is provided an endoscope which includes: an exterior member formed by resin molding; a through hole formed in the exterior member and having a first center axis; an operating member disposed in the through hole, the operating member having a moving member configured to move along a predetermined axis; and a connecting member fixedly mounted in the through hole, the connecting member being disposed so as to make the predetermined axis of the operating member intersect with the first center axis of the through hole at a preliminarily set angle.

According to another aspect of the present invention, there is provided a case body provided with an operating member having a moving member configured to move along a predetermined axis. The case body includes: an exterior member formed by resin molding; a through hole formed in the exterior member and having a first center axis, wherein the operating member is disposed in the through hole; and a connecting member fixedly mounted in the through hole, the connecting member being disposed so as to make the predetermined axis of the operating member intersect with the first center axis of the through hole at a preliminarily set angle.

DETAILED DESCRIPTION OF THE PREFERRED EMBODIMENTS

Figure 1A:
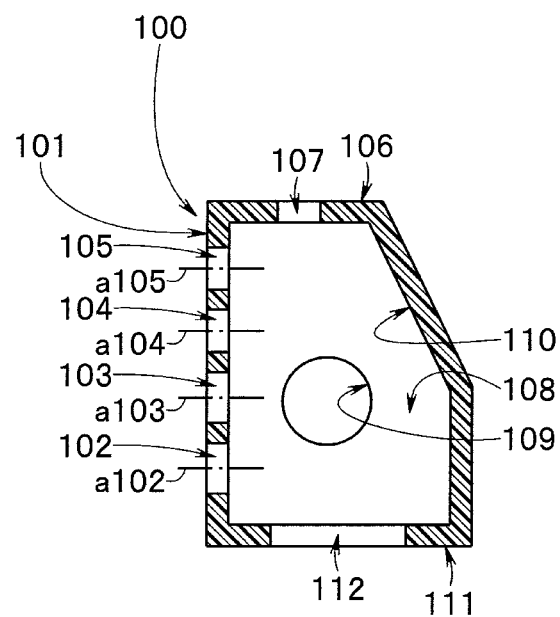
FIG. 1A is a diagram for illustrating a case body.
Figure 1B:
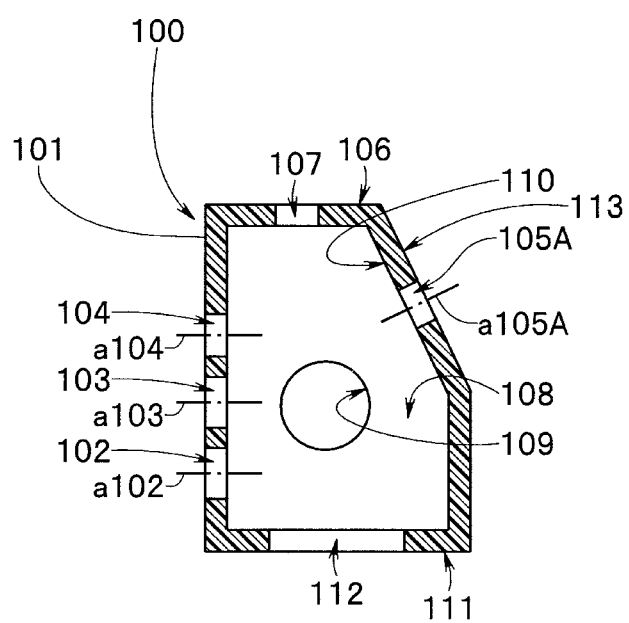
FIG. 1B is a diagram for illustrating a configurational example of the case body by which operability can be enhanced.
Figure 1C:
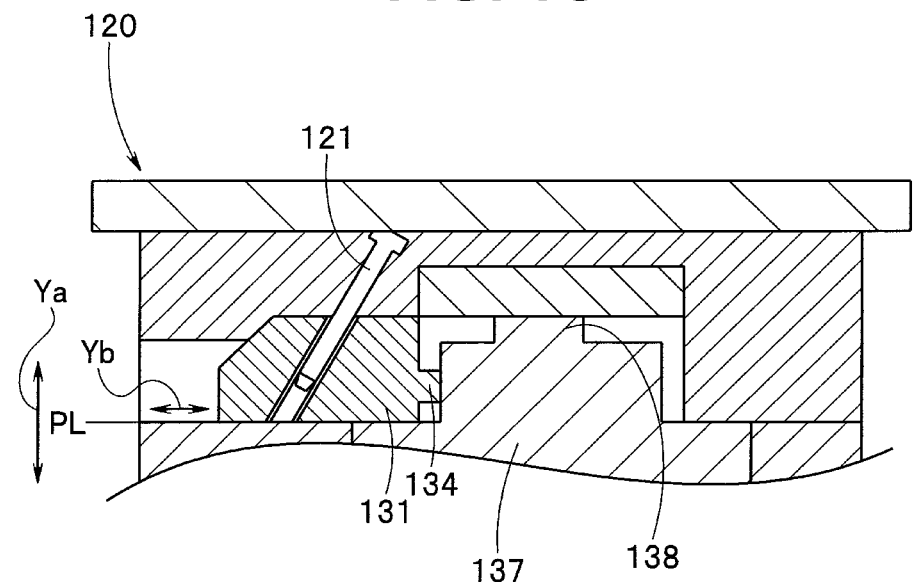
FIG. 1C is a diagram showing a mold which includes a slide core which forms a front plate side.
Figure 1D:
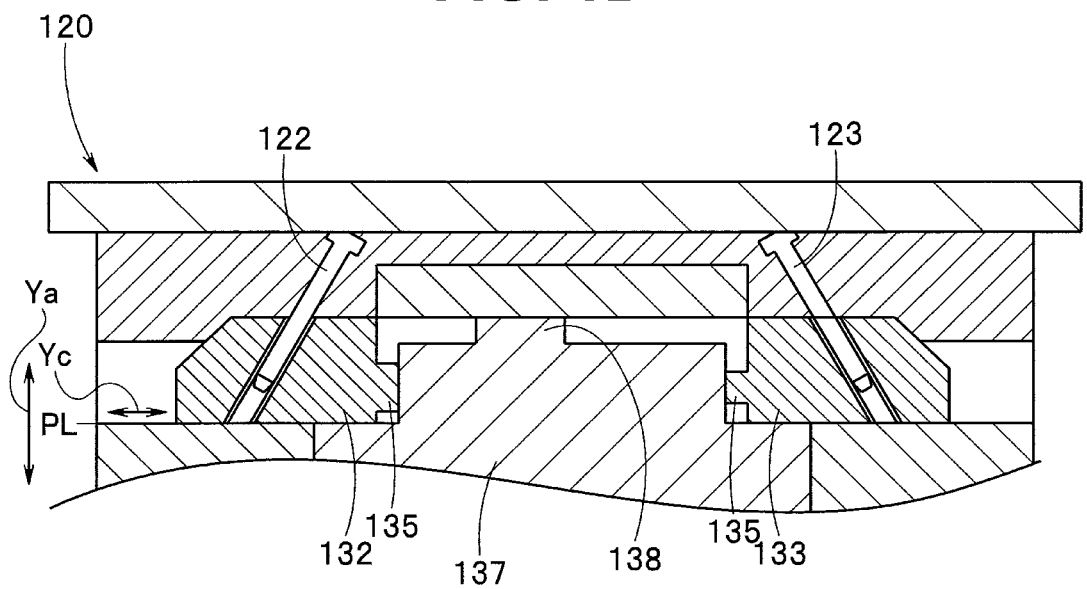
FIG. 1D is a diagram showing a mold which includes a slide core which forms an upper plate side, and a slide core which forms a lower plate side.

Hereinafter, embodiments of the present invention are described with reference to drawings.

In the respective drawings used in the description made hereinafter, for the sake of setting sizes of respective components legible in the drawings, the scales of the respective components are made different from each other. In other words, the present invention is not limited to the number and the amounts of components, the shapes of the components, ratios between the sizes of the components, and the relative positional relationships among the respective components described in the drawings.

Figure 2:
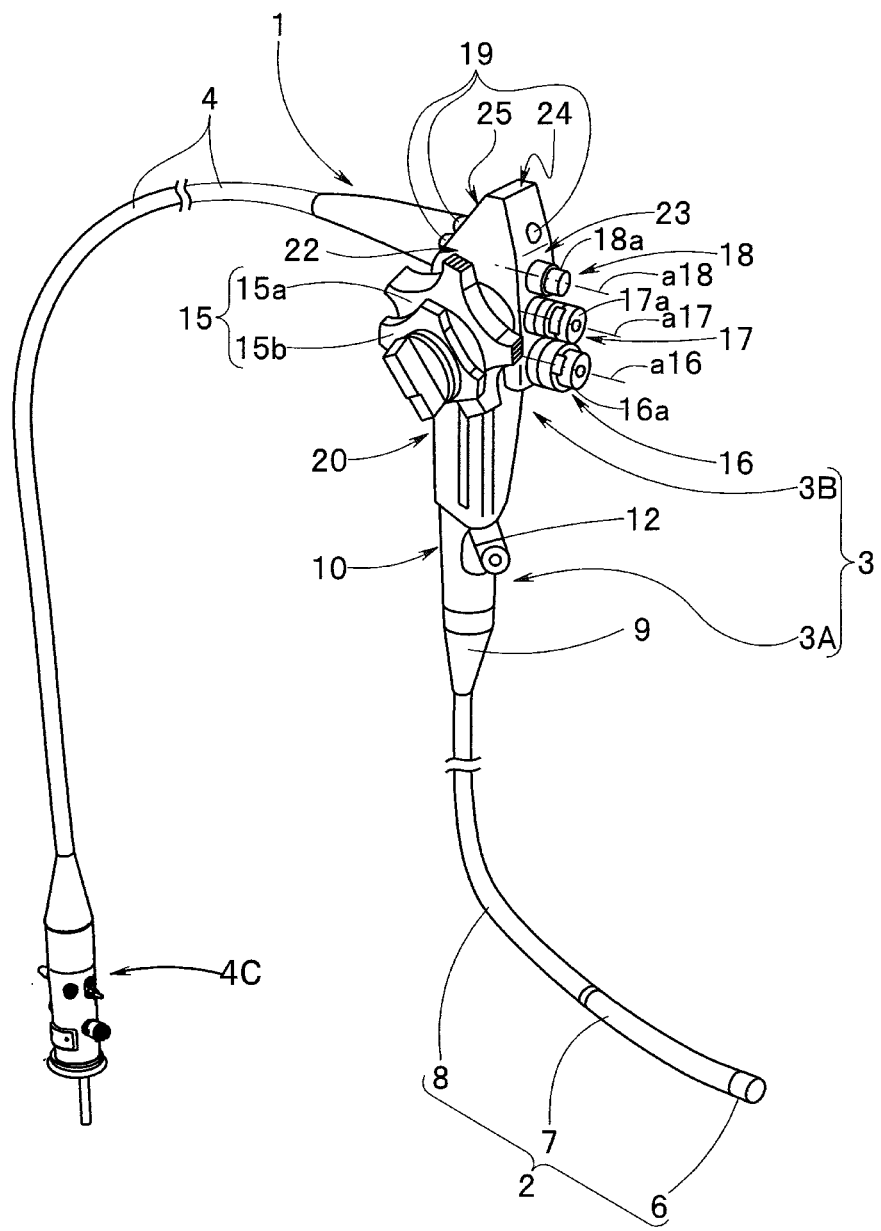
FIG. 2 is a diagram for illustrating an endoscope which includes an exterior member made of resin.

An endoscope 1 shown in FIG. 2 includes an insertion section 2, an operation section 3 and a universal cable 4. An endoscope connector 4C is mounted on a proximal end portion of the universal cable 4. The endoscope connector 4C is detachably connected to an external apparatus such as a camera control unit. The operation section 3 and the endoscope connector 4C each include an exterior member.

The insertion section 2 is a long member which is inserted into a site which is an observation target. The insertion section 2 is formed by connecting a distal end portion 6, a bending portion 7, and a flexible tube portion 8.

For example, an illumination optical system which includes a light guide (not shown) and an image pickup apparatus (not shown) which includes an image pickup device are incorporated in the distal end portion 6. The bending portion 7 bends, for example, in four directions, that is, in upward, downward, leftward and rightward directions. The flexible tube portion 8 is a long tubular member having flexibility. The bending portion 7 may be a bending portion which bends, for example, in two directions, that is, upward and downward directions.

The operation section 3 is formed by integrally combining an operation section distal end portion 3A and an operation section body 3B, for example.

The operation section distal end portion 3A includes a first exterior body 10 which is an exterior member. A proximal end portion of the insertion section 2 is connected to a distal end side of the first exterior body 10 by way of a bend preventing member 9, for example. A treatment instrument insertion opening 12 is formed on a side portion of a proximal end side of the first exterior body 10.

The operation section body 3B which is a case body includes a second exterior body 20. A bending operation portion 15 is disposed on one surface 22 of the second exterior body 20. For example, a bending operation knobs 15a, 15b for performing a bending operation of the bending portion 7 are fixedly mounted on the bending operation portion 15.

On one side surface 23 which is disposed adjacently to the one surface 22, an air/water feeding button 16 and a suction button 17 which are operating members, a push button switch 18 which is an operating member and an electric switch, and electric switches 19 are mounted. A button portion 16a which is a moving member of the air/water feeding button 16 moves in an advancing and retracting manner along an air/water feeding button center axis a16 which is a predetermined axis in the air/water feeding button 16. A button portion 17a which is a moving member of the suction button 17 moves in an advancing and retracting manner along a suction button center axis a17 which is a predetermined axis in the suction button 17.

The electric switches 19 and the push button switch 18 differ from each other in type. Symbol 24 indicates one end surface, and the one end surface 24 is disposed adjacently to the one surface 22 and the one side surface 23. The one end surface 24 is a surface of the second exterior body 20 on a proximal end side. Symbol 25 indicates the other side surface. Two electric switches 19 are mounted on the other side surface 25.

Among a plurality of functions which the endoscope 1 has, for example, a function of switching an observation mode, a freezing function, a release function, a function of switching focusing of the endoscope are allocated to the push button switch 18 and three electric switches 19.

Figure 3:
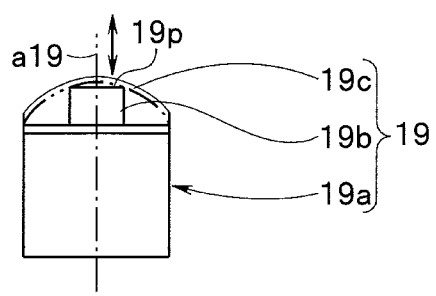
FIG. 3 is a diagram showing one example of an electric switch.

As shown in FIG. 3, the electric switch 19 is mainly formed of a switch body 19a and a moving member 19b. The moving member 19b is held in a watertight state by a cover 19c indicated by a double-dashed chain line. When an operation surface 19p of the moving member 19b is pressed by way of the cover 19c, the moving member 19b moves in an advancing and retracting manner along a switch center axis a19 which is a predetermined axis in the electric switch 19. The moving member 18a of the push button switch 18 moves in an advancing and retracting manner along a button switch center axis a18 which is a predetermined axis in the push button switch 18.

In the present embodiment, each of the air/water feeding button center axis a16, the suction button center axis a17, the button switch center axis a18, and the switch center axis a19 is an operating member center axis, and is also described as a second axis.

The second exterior body 20 is described with reference to FIG. 4A to FIG. 4D.

Figure 4A:
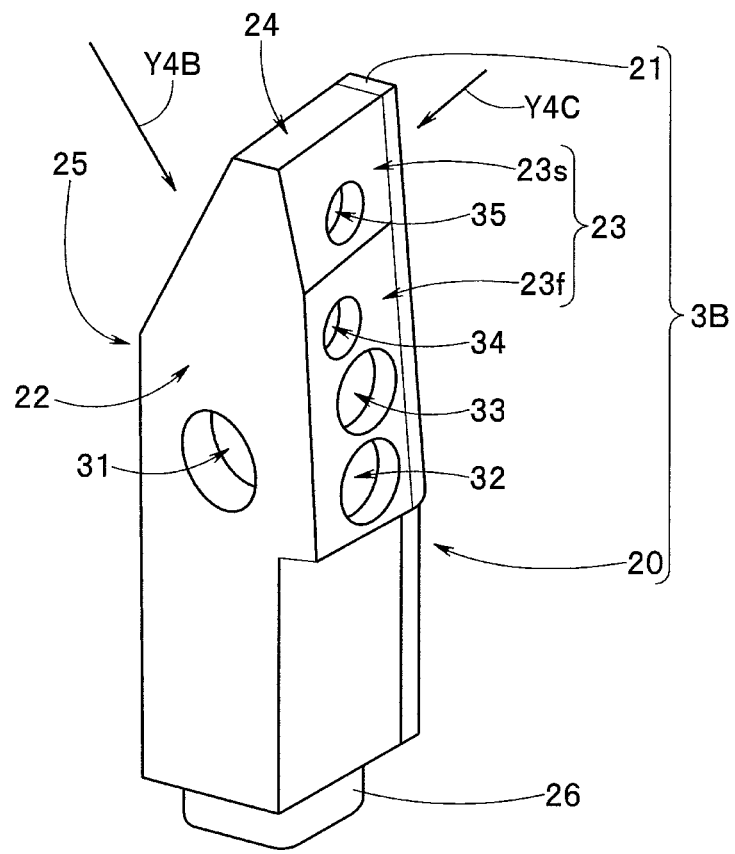
FIG. 4A is a schematic view for illustrating an operation section body which includes the exterior member and a lid body.
Figure 4B:
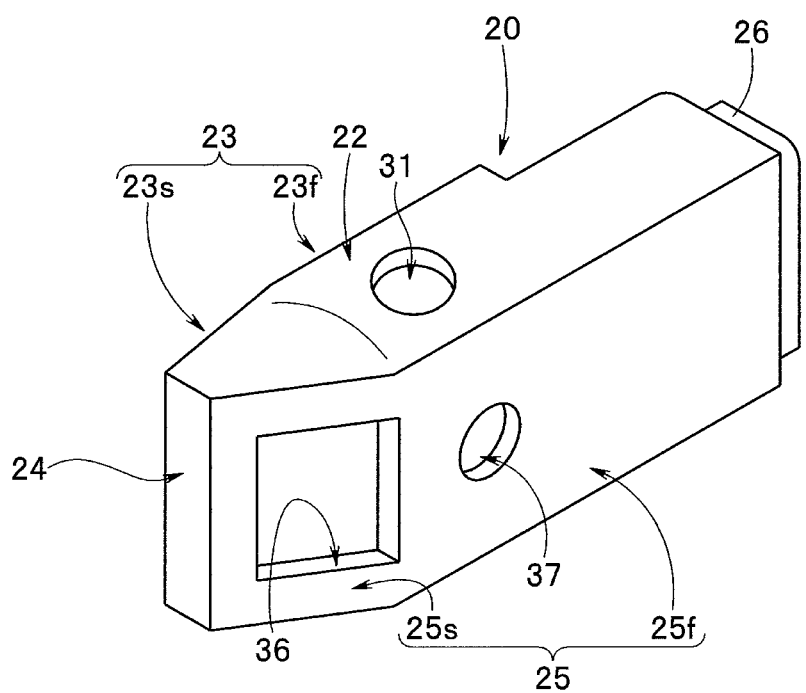
FIG. 4B is a perspective view of the exterior member as viewed from a direction of an arrow 4B in FIG. 4A.
Figure 4C:
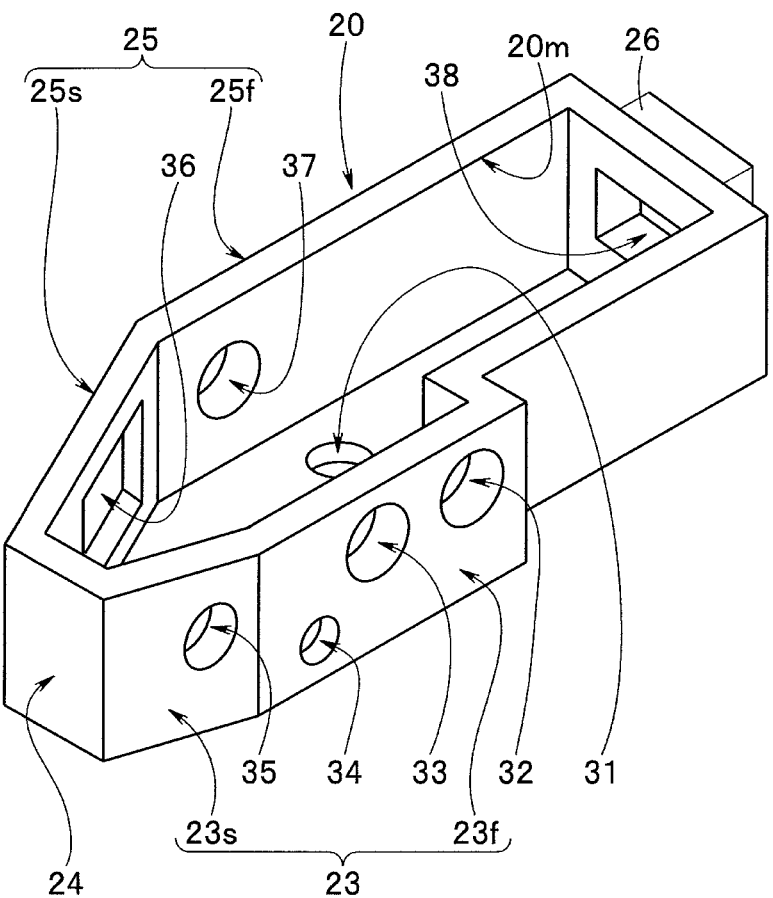
FIG. 4C is a perspective view of the exterior member in a state where the lid body is removed from the exterior member as viewed in a direction of an arrow 4C in FIG. 4A.

As shown in FIG. 4A, the operation section body 3B includes the second exterior body 20 which is an exterior member and a lid body 21. The lid body 21 has a plate shape. The lid body 21 is disposed so as to close an opening 20m of the second exterior body 20.

As shown in FIG. 4A to FIG. 4D, a plurality of through holes 31, 32, 33, 34, 35, 36, 37, and 38 are formed in the second exterior body 20.

The hole 31 for operation section support shaft having, for example, a circular cross-sectional shape is formed in the one surface 22 of the second exterior body 20. The hole 31 for operation section support shaft has a hole center axis a31 for support shaft which forms a first center axis. A frame shaft (not shown) of the bending operation portion 15 is disposed in the hole 31 for operation section support shaft. The hole 32 for air/water feeding button, the hole 33 for suction button, the hole 34 for push button switch, and the hole 35 for electric switch each having, for example, a circular cross-sectional shape are formed in the one side surface 23 of the second exterior body 20. The holes 32 to 35 are formed as operating member arranging holes (hereinafter also described as arranging holes).

The hole 32 for air/water feeding button has an air/water feeding hole center axis a32 which forms the first center axis. The hole 33 for suction button has a suction hole center axis a33 which forms the first center axis. The hole 34 for push button switch has a button switch hole center axis a34 which forms the first center axis. The hole 35 for electric switch has an electric switch hole center axis a35 which forms the first center axis.

The hole 35 for electric switch is a connecting member arranging hole, and is formed on a slanted surface portion 23s of the one side surface 23. Symbol 23f indicates a flat surface portion. The one side surface 23 has the slanted surface portion 23s and the flat surface portion 23f.

The other side surface 25 of the second exterior body 20 has a slanted surface portion 25s and a flat surface portion 25*f*. The angular hole 36 for electric switch having, for example, rectangular cross-sectional shape is formed in the slanted surface portion 25*s*. The angular hole 36 for electric switch is formed as a connecting member arranging hole. The hole 37 for cord having, for example, a circular cross-sectional shape is formed in the flat surface portion 25*f*. The universal cable 4 is made to pass through the hole 37 for cord.

The angular hole 36 for electric switch has an electric switch angular hole center axis a36 which forms the first center axis. The hole 37 for cord has a cord hole center axis a37 which forms the first center axis.

Symbol 26 indicates a connecting protruding portion. An end surface of the connecting protruding portion 26 forms a surface opposite to the one end surface 24. An end portion of the first exterior body 10 is fixedly mounted on the connecting protruding portion 26 in a watertight manner Symbol 38 indicates a frame hole. The frame hole 38 has, for example, a rectangular cross-sectional shape, and has a frame hole center axis a38 which forms the first center axis. A frame (not shown) having a thin plate shape is disposed in the frame hole 38.

A bending operation mechanism which includes support shafts, sprockets, chains, bending wires and the like not shown is fixedly mounted on the frame. The frame is fixedly mounted in the first exterior body 10 and in the second exterior body 20.

Figure 4D:
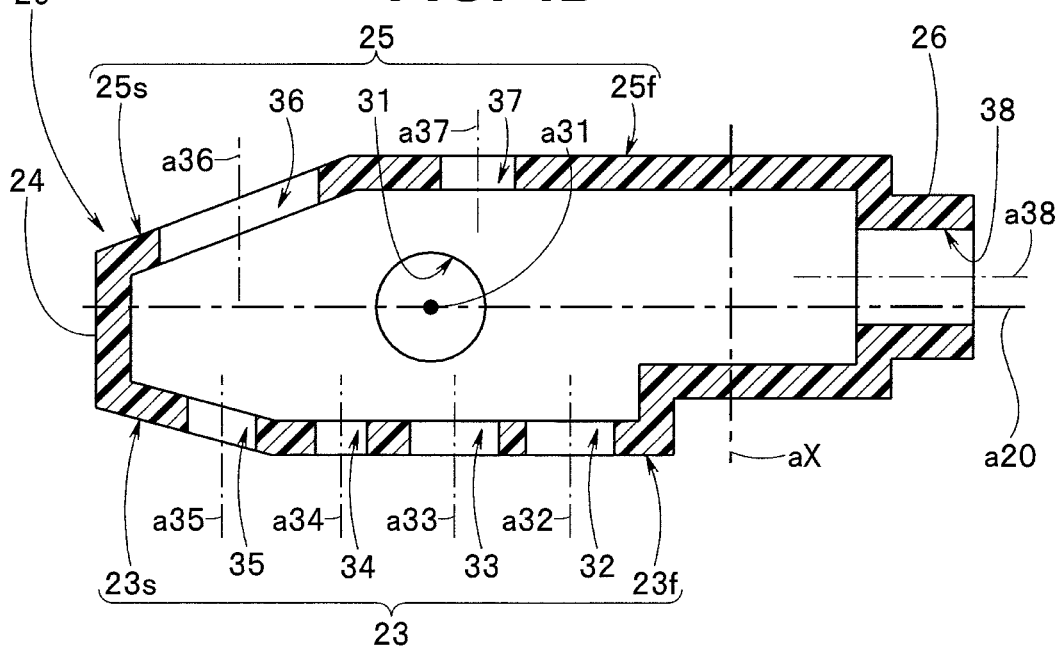
FIG. 4D is a diagram for illustrating a relationship between respective holes formed in the exterior member and a longitudinal direction axis and an orthogonal axis.

In FIG. 4D, symbol a20 indicates a longitudinal direction axis of the second exterior body 20. In the present embodiment, the longitudinal direction axis a20 is orthogonal to the hole center axis a31 for support shaft of the hole 31 for operation section support shaft. Symbol aX indicates an orthogonal axis. The orthogonal axis aX is orthogonal to the longitudinal direction axis a20.

The flat surface portion 23*f* of the one side surface 23 and the flat surface portion 25*f* of the other side surface 25 described previously are flat surfaces extending along the longitudinal direction axis a20. The frame hole center axis a38 is arranged parallel to the longitudinal direction axis a20.

The air/water feeding hole center axis a32 of the hole 32 for air/water feeding button, the suction hole center axis a33 of the hole 33 for suction button, the button switch hole center axis a34 of the hole 34 for push button switch, the electric switch hole center axis a35 of the hole 35 for electric switch, the electric switch angular hole center axis a36 of the angular hole 36 for electric switch, and the cord hole center axis a37 of the hole 37 for cord are arranged parallel to the orthogonal axis aX.

Each of the air/water feeding hole center axis a32, the suction hole center axis a33, the button switch hole center axis a34, the electric switch hole center axis a35, and the electric switch angular hole center axis a36 is an arranging hole center axis.

Figure 5A:
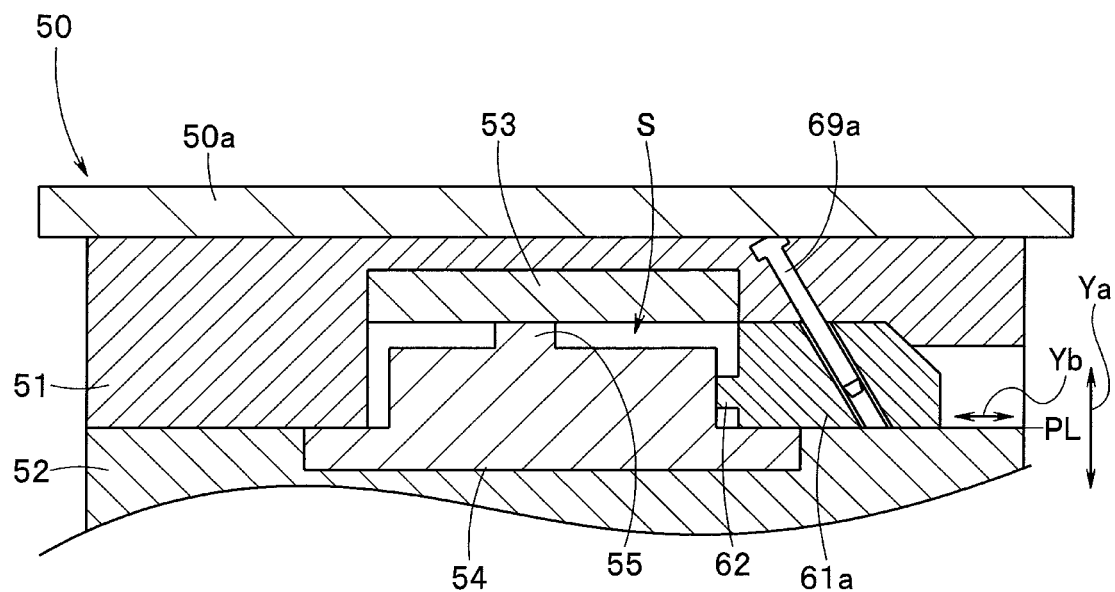
FIG. 5A is a diagram for illustrating a mold for forming a second exterior body by molding, and mainly illustrating a movable side block where a protruding portion for support shaft is formed, and a first slide core side where a protruding portion for forming a frame hole is disposed.
Figure 5B:
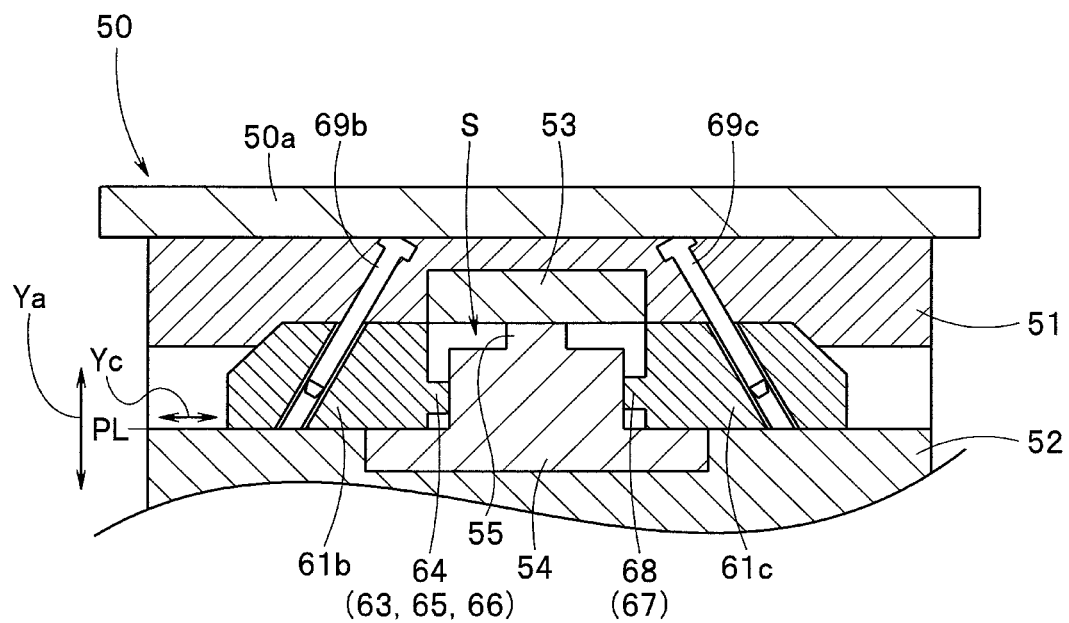
FIG. 5B is a diagram for illustrating a mold for forming the second exterior body by molding, and illustrating a second slide core side where the second slide core side is movable in a first direction, and protruding portions for forming a hole for air/water feeding button, a hole for suction button, a hole for push button switch and a hole for electric switch are formed, and a third slide core side where the third slide core side is movable in the first direction, and protruding portions for forming an angular hole for electric switch and a hole for cord are formed.
Figure 5C:
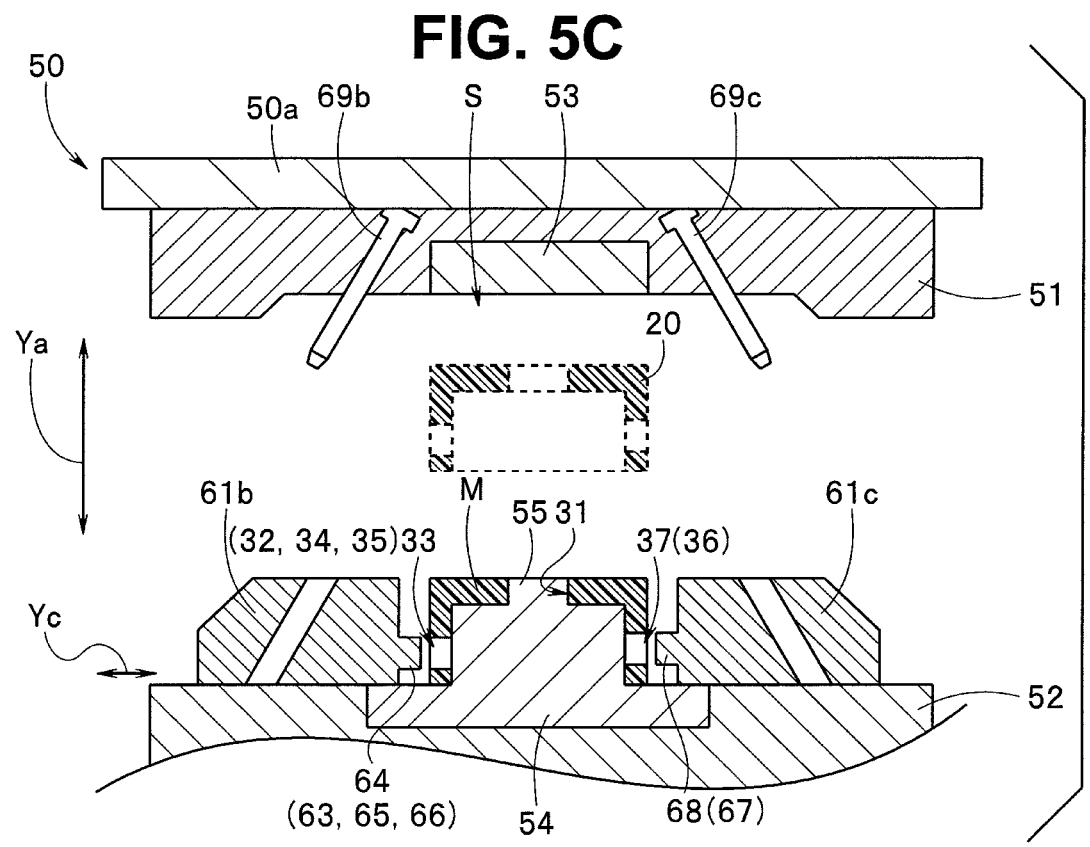
FIG. 5C is a diagram showing the mold for forming the second exterior body by molding in an open state, and illustrating a molded product remaining in a movable side block and the second exterior body removed from the movable side block.

The second exterior body 20 described above is formed by resin molding using a mold 50 shown in FIG. 5A to FIG. 5C.

As shown in FIG. 5A, FIG. 5B, and FIG. 5C, the mold 50 includes a fixed mold 51 and a movable mold 52. A fixed side block 53 which forms an outer surface of the one surface 22 of the second exterior body 20 is mounted on the fixed mold 51.

A movable side block 54 which forms an inner surface of the one surface 22 is mounted on the movable mold 52. A protruding portion 55 for support shaft for forming the hole 31 for operation section support shaft is formed on the movable side block 54.

Symbol 61*a* indicates a first slide core, symbol 61*b* indicates a second slide core, and symbol 61*c* indicates a third slide core.

A protruding portion 62 for forming the frame hole 38 is formed on the first slide core 61*a*. Protruding portions 63, 64, 65, and 66 for forming the hole 32 for air/water feeding button, the hole 33 for suction button, the hole 34 for push button switch, and the hole 35 for electric switch are formed on the second slide core 61*b*. Protruding portions 67, 68 for respectively forming the angular hole 36 for electric switch and the hole 37 for cord are formed on the third slide core 61*c*.

Symbol 69*a* indicates a first angular pin, symbol 69*b* indicates a second angular pin, and symbol 69*c* indicates a third angular pin. Symbol 50*a* indicates a fixed side mounting plate.

In the present embodiment, when the movable mold 52 of the mold 50 moves in an opening direction of an arrow Ya so that the movable mold 52 changes from a closed state shown in FIG. 5A and FIG. 5B to an open state shown in FIG. 5C, the first slide core 61*a* moves in an outward direction of an arrow Yb by the first angular pin 69*a*. The second slide core 61*b* moves in an outward direction of an arrow Yc by the second angular pin 69*b*, and the third slide core 61*c* moves in the outward direction of the arrow Yc by the third angular pin 69*c*.

When the movable mold 52 of the mold 50 moves in a closing direction of the arrow Ya so that the movable mold 52 changes from the open state to the closed state, contrary to the above-mentioned movement, the first slide core 61*a* moves in an inward direction of the arrow Yb by the first angular pin 69*a*. The second slide core 61*b* moves in an inward direction of the arrow Yc by the second angular pin 69*b*, and the third slide core 61*c* moves in the inward direction of the arrow Yc by the third angular pin 69*c*.

The direction of the arrow Ya which is an opening/closing direction of the mold in the present embodiment agrees with an extending direction of the hole center axis a31 for support shaft of the hole 31 for operation section support shaft which the second exterior body 20 formed by molding using the mold 50 has. The direction of the arrow Yb which is a moving direction of the first slide core 61*a* agrees with the longitudinal direction axis a20 of the second exterior body 20 formed by molding using the mold 50. The direction of the arrow Yc which is a moving direction of the second slide core 61*b* and the third slide core 61*c* agrees with the orthogonal axis aX of the second exterior body 20 formed by molding using the mold 50.

An exterior body molding space (hereinafter, abbreviated as a sealed space) S which is formed in the mold 50 in a mold closed state shown in FIG. 5A and FIG. 5B is filled with molten resin. The resin filled in the sealed space S is cured by cooling.

After a predetermined time period elapses, the mold 50 is brought into an open state shown in FIG. 5C. In this case, the movable mold 52 moves in an opening direction of the arrow Ya in the drawing with respect to the fixed mold 51. As a result, the slide cores 61*a*, 61*b*, and 61*c* are moved along with the movement of the movable mold 52, and a cured molded product M remains in the movable side block 54.

Then, an ejector pin not shown which is provided to the mold 50 is operated. As a result, the molded product M remaining on the movable side block 54 is removed from the movable side block 54, and the second exterior body 20 indicated by a broken line is obtained.

A relationship between the operating members and the respective holes is described with reference to FIG. 6 to FIG. 8C.

Figure 6:
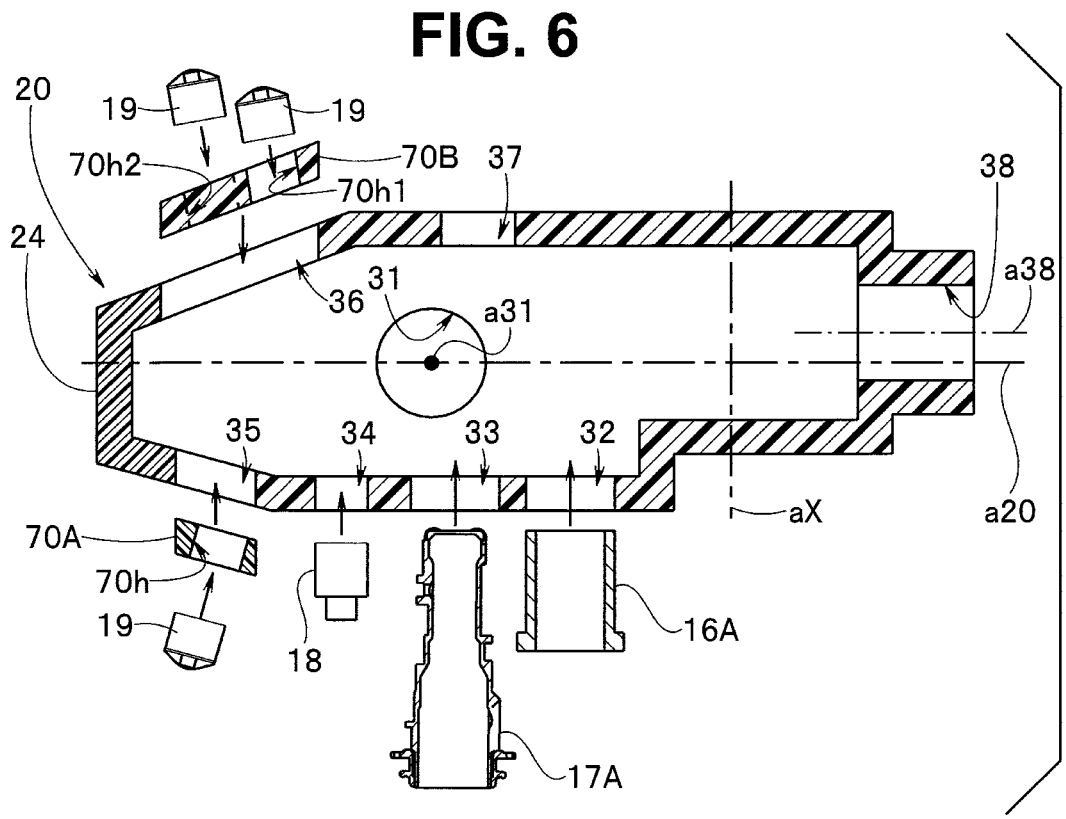
FIG. 6 is a diagram for illustrating a relationship between a plurality of holes formed in the exterior member and operating members disposed in the respective holes.

As shown in FIG. 6, an air/water feeding pipe sleeve 16A is disposed and is fixedly mounted in the hole 32 for air/water feeding button in a watertight manner A suction pipe sleeve 17A is disposed and is fixedly mounted in the hole 33 for suction button in a watertight manner. An exterior portion of the push button switch 18 is disposed and is fixedly mounted in the hole 34 for push button switch in a watertight manner. The electric switch 19 is disposed in the hole 35 for electric switch together with a first connecting member 70A. Two electric switches 19 are disposed in the angular hole 36 for electric switch together with a second connecting member 70B.

Figure 7A:
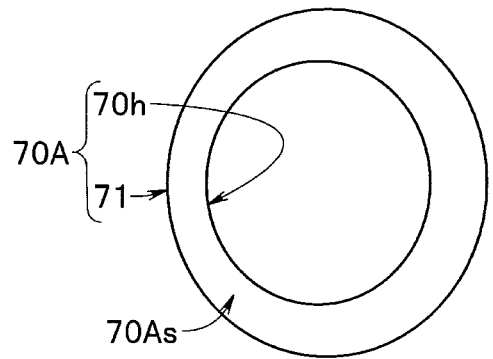
FIG. 7A is a diagram for illustrating a connecting member having a circular columnar shape which includes one switch fixing hole.
Figure 7B:
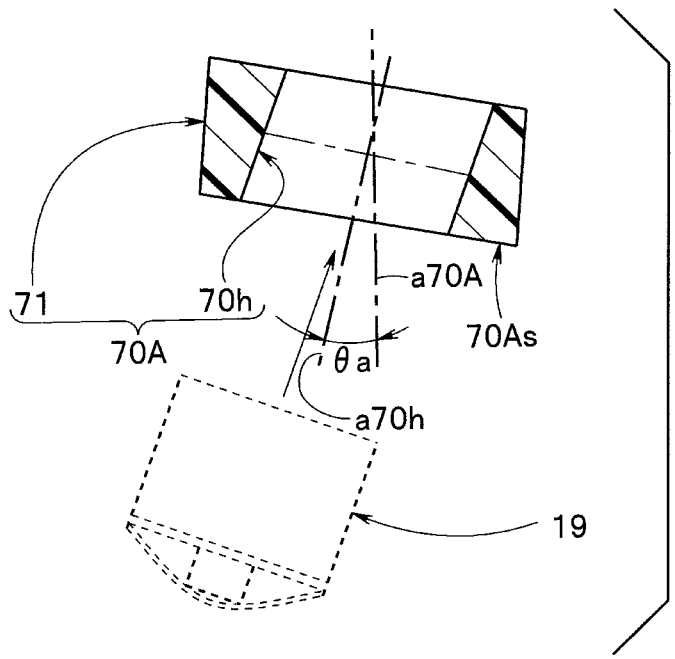
FIG. 7B is a diagram for illustrating a relationship between an electric switch and the switch fixing hole formed in the connecting member.

As shown in FIG. 7A and FIG. 7B, the first connecting member 70A has a switch fixing hole 70h and an outer peripheral surface portion 71. The switch fixing hole 70h is an operating member fixing hole. The outer peripheral surface portion 71 is an outer surface of the first connecting member 70A and is fixed to an inner surface of the hole 35 for electric switch. An outer diameter of the outer peripheral surface portion 71 is set such that the outer peripheral surface portion 71 is accommodated in the hole 35 for electric switch.

In FIG. 7B, symbol a70A indicates a member center axis. The member center axis a70A forms a second center axis, and is parallel to the outer peripheral surface portion 71 of the first connecting member 70A. The first connecting member 70A is a circular columnar member having the outer peripheral surface portion 71. Both ends of the circular columnar member are formed into slanted surfaces 70As. One slanted surface 70As is substantially coplanar with an outer surface of the slanted surface portion 23s, and the other slanted surface 70As is substantially coplanar with an inner surface of the slanted surface portion 23s.

The switch fixing hole 70h is a through hole formed along a fixing hole center axis a70h. The electric switch 19 is disposed in the switch fixing hole 70h. The fixing hole center axis a70h forms a third center axis.

An inner diameter of the switch fixing hole 70h is set such that the switch body 19a is accommodated in the switch fixing hole 70h. In the present embodiment, the fixing hole center axis a70h of the switch fixing hole 70h is set orthogonal to the slanted surface 70As. Accordingly, the fixing hole center axis a70h and the member center axis a70A of the first connecting member 70A intersect with each other at an angle θa. The angle θa is an acute angle.

Before the first connecting member 70A is disposed in the hole 35 for electric switch, the electric switch 19 is disposed in the hole 70h for electric switch in a preliminarily set state as shown in FIG. 7B. The electric switch 19 is integrally and fixedly mounted in the hole 70h for electric switch in a watertight manner.

Figure 7C:
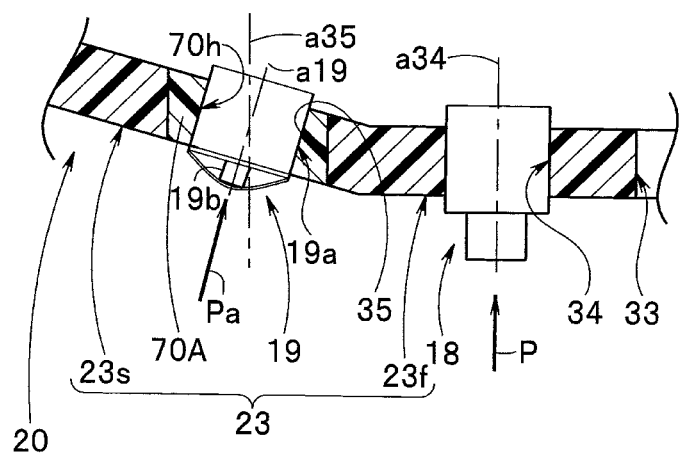
FIG. 7C is a diagram for illustrating an operation direction of the electric switch disposed in the connecting member which is fixedly mounted in a hole for electric switch formed in a slanted surface portion and an operation direction of a push button switch fixedly mounted in a hole for push button switch formed on a flat surface portion.

As shown in FIG. 7C, the first connecting member 70A where the electric switch 19 is integrally fixedly mounted in the hole 70h for electric switch is disposed in the hole 35 for electric switch. In such a configuration, the member center axis a70A of the first connecting member 70A and the electric switch hole center axis a35 are arranged parallel to each other or coaxially. Then, the first connecting member 70A is fixedly mounted in the hole 35 for electric switch in a watertight manner. In such a configuration, the fixing hole center axis a70h is arranged in an intersecting manner with the electric switch hole center axis a35 at a preliminarily set angle θa.

In the present embodiment, when the moving member 19b of the electric switch 19 fixedly mounted in the switch fixing hole 70h is pushed in a direction of an arrow Pa intersecting with the electric switch hole center axis a35, the moving member 19b moves along the switch center axis a19. In other words, an operating direction of the push button switch 18 and an operating direction of the electric switch 19 differ from each other.

Figure 8A:
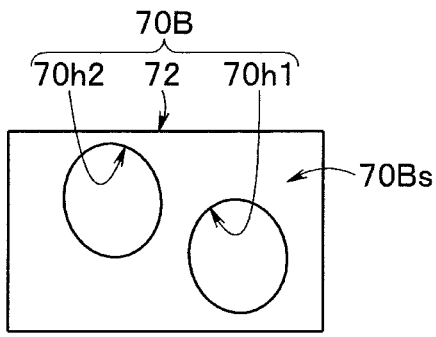
FIG. 8A is a diagram for illustrating a connecting member having a polygonal columnar shape which includes two switch fixing holes.
Figure 8B:
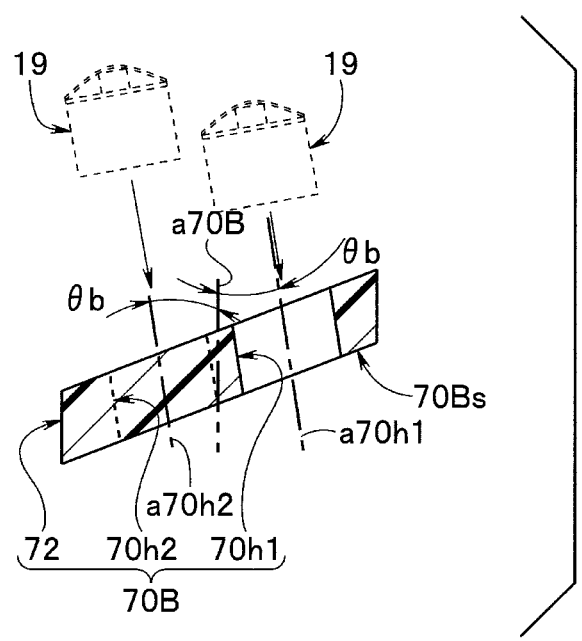
FIG. 8B is a diagram for illustrating a relationship between electric switches and the switch fixing holes formed in the connecting member.

As shown in FIG. 8A and FIG. 8B, the second connecting member 70B has a rectangular surface portion 72, a first switch fixing hole 70h1, and a second switch fixing hole 70h2. Each of the first switch fixing hole 70h1 and the second switch fixing hole 70h2 forms an operating member fixing hole. The rectangular surface portion 72 is an outer surface of the second connecting member 70B and is fixed to an inner surface of the angular hole 36 for electric switch. A rectangular profile of the rectangular surface portion 71 is set such that the rectangular surface portion 71 is accommodated in the angular hole 36 for electric switch.

In FIG. 8B, symbol a70B indicates a member center axis. The member center axis a70B forms a second center axis, and is parallel to the rectangular surface portion 72 of the second connecting member 70B. The second connecting member 70B is an angular columnar member having the rectangular surface portion 72. Both ends of the angular columnar member are formed into slanted surfaces 70Bs. One slanted surface 70Bs is substantially coplanar with an outer surface of the slanted surface portion 25s, and the other slanted surface 70Bs is substantially coplanar with an inner surface of the slanted surface portion 25s.

The first switch fixing hole 70h1 is a through hole formed along a first fixing hole center axis a70h1 which forms a third center axis. The electric switch 19 is disposed in the first switch fixing hole 70h1. The second switch fixing hole 70h2 is a through hole formed along a second fixing hole center axis a70h2 which forms a third center axis. The electric switch 19 is disposed in the second switch fixing hole 70h2. Inner diameters of the switch fixing holes 70h1, 70h2 are set such that the switch bodies 19a are accommodated in the switch fixing holes 70h1, 70h2.

In the present embodiment, the first fixing hole center axis a70h1 of the first switch fixing hole 70h1 and the second fixing hole center axis a70h2 of the second switch fixing hole 70h2 are set orthogonal to the slanted surface 70Bs. In other words, the first fixing hole center axis a70h1 and the second fixing hole center axis a70h2 intersect with the member center axis a70B of the second connecting member 70B at the same angle θb. The angle θb is an acute angle.

Before the second connecting member 70B is disposed in the angular hole 36 for electric switch, the electric switches 19 are respectively disposed in the first switch fixing hole 70h1 and the second switch fixing hole 70h2 in a preliminarily set state as shown in FIG. 8B. The electric switches 19 are integrally and fixedly mounted in the first switch fixing hole 70h1 and the second switch fixing hole 70h2 in a watertight manner.

Figure 8C:
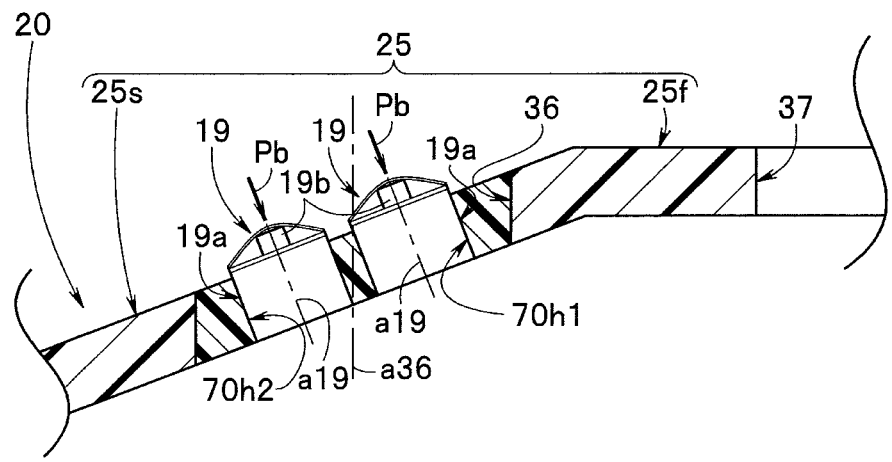
FIG. 8C is a diagram for illustrating an operation direction of two electric switches disposed on the connecting member which is fixedly mounted in an angular hole for electric switch formed in the slanted surface portion.

As shown in FIG. 8C, the second connecting member 70B where the electric switches 19 are respectively integrally fixedly mounted in the switch fixing holes 70h1, 70h2 is disposed in the angular hole 36 for electric switch. In such a configuration, the member center axis a70B of the second connecting member 70B and the electric switch angular hole center axes a36 are arranged parallel to each other or coaxially. Then, the second connecting member 70B is fixedly mounted in the angular hole 36 for electric switch in a watertight manner. In such a configuration, the fixing hole center axes a70h1, a70h2 are arranged in an intersecting manner with the electric switch angular hole center axis a36 at a preliminarily set angle θb.

In the present embodiment, the arrangement positions of two electric switches 19 are set by taking into account operability and prevention of an erroneous operation.

In this manner, in mounting the electric switches 19 on the slanted surface portions 23s, 25s respectively, the hole 35 for electric switch having the electric switch hole center axis a35 parallel to the orthogonal axis aX is formed in the slanted surface portion 23s, and the angular hole 36 for electric switch having the electric switch angular hole center axis a36 parallel to the orthogonal axis aX is formed in the slanted surface portion 25s.

The electric switch hole center axis a35 and the electric switch angular hole center axis a36 of the second exterior body 20 are made to agree with the moving directions of the slide cores which move along with an open/close operation of the mold 50.

With such a configuration, the hole 35 for electric switch and the angular hole 36 for electric switch can be formed in the second exterior body 20 in addition to the hole 32 for air/water feeding button, the hole 33 for suction button, the hole 34 for push button switch, and the hole 37 for cord without adopting a complicated mold structure.

The electric switch 19 is fixedly mounted in the switch fixing hole 70h of the first connecting member 70A and, thereafter, the first connecting member 70A is fixedly mounted in the hole 35 for electric switch. On the other hand, the electric switches 19 are respectively fixedly mounted in the first switch fixing hole 70h1 and the second switch fixing hole 70h2 of the second connecting member 70B and, thereafter, the second connecting member 70B is fixedly mounted in the angular hole 36 for electric switch.

With such a configuration, the electric switches 19 can be disposed at desired positions on the slanted surface portions 23s, 25s of the second exterior body 20 while assigning priority on operability. In one connecting member 70B, the plurality of electric switches 19 can be disposed on the slanted surface portion 25s of the second exterior body 20 at desired positions by taking into account operability and prevention of an erroneous operation.

The shape of the connecting members 70A, 70B is not limited to the circular columnar shape and the angular columnar shape described above, and may be a columnar shape having other cross-sectional shapes.

The number and the arrangement positions of the switch fixing holes formed in the connecting members 70A, 70B, and an intersecting angle between the fixing hole center axis and the member center axis are not limited to values in the above-mentioned embodiment. Specifically, a plurality of switch fixing holes may be formed in the connecting member 70A having a circular columnar shape, or one switch fixing hole may be formed in the connecting member 70B having an angular columnar shape. Three or more switch fixing holes 70h may be formed in the connecting members 70A, 70B.

With such a configuration, the electric switches can be disposed at desired positions while assigning priority on operability and an operating direction.

In the above-mentioned embodiment, both end surfaces of the connecting members 70A, 70B each formed of a columnar member are slanted surfaces, and these slanted surfaces are set such that the slanted surfaces are made coplanar with an outer surface and an inner surface of the slanted surface portion in which the mounting hole is formed. However, both end surfaces of the columnar member are not limited to slanted surfaces which are coplanar with an outer surface and an inner surface of the slanted surface portions, and can be suitably set.

The connecting members 70A, 70B in the above-mentioned embodiment have the switch fixing holes 70h, 70h1, 70h2 in which the electric switches 19 are fixedly mounted as the operating members. However, the operating members which are fixedly mounted in the operating member fixing holes formed in the connecting members 70A, 70B are not limited to the electric switches 19. In other words, a hole for fixing air/water feeding button, a hole for fixing suction button and a hole for fixing push button switch may be formed in the connecting members.

With such a configuration, the connecting member on which the air/water feeding pipe sleeve 16A is fixedly mounted, the connecting member on which the suction pipe sleeve 17A is fixedly mounted, and the connecting member on which the exterior portion of the push button switch 18 are fixedly mounted are fixedly mounted in the corresponding operating member arranging holes formed in the second exterior body 20.

Accordingly, the arrangement positions and the operation directions of the air/water feeding button 16, the suction button 17, and the push button switch 18 can be freely set without adopting a complicated mold structure.

An opening for treatment instrument channel may be formed on a second exterior body 20 side. The operating members which are mounted on the second exterior body 20 are not limited to the air/water feeding button 16, the suction button 17, the push button switch 18, and the electric switches 19 described above, and one button for fluid control and a plurality of electric switches may be mounted on the second exterior body 20.

In the above-mentioned embodiment, the hole 32 for air/water feeding button, the hole 33 for suction button, the hole 34 for push button switch, the hole 35 for electric switch, the angular hole 36 for electric switch, and the hole 37 for cord are formed in the second exterior body 20. The air/water feeding hole center axis a32, the suction hole center axis a33, the button switch hole center axis a34, the electric switch hole center axis a35, the electric switch angular hole center axis a36, and the cord hole center axis a37 are arranged parallel to the orthogonal axis aX.

Another second exterior body having different configuration is described.

Figure 9A:
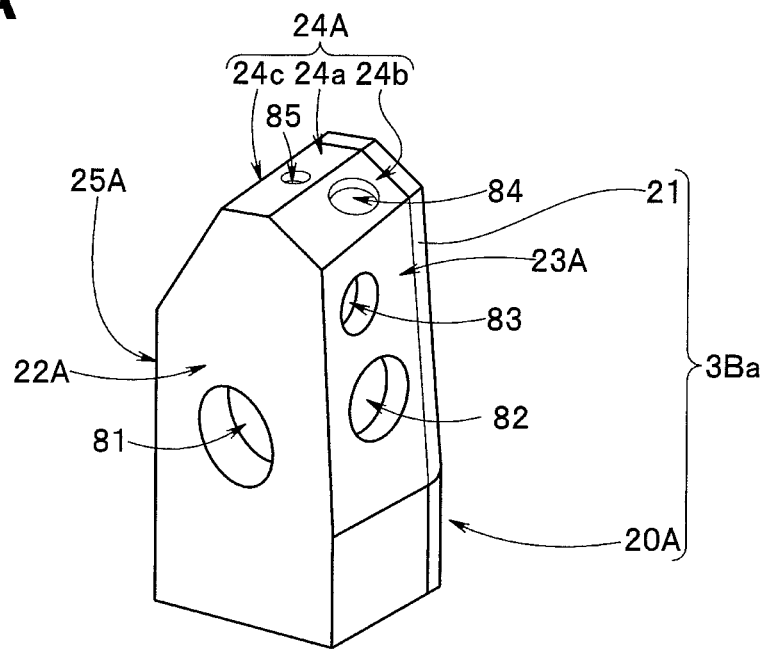
FIG. 9A is a schematic view for illustrating another configurational example of the operation section body which includes an exterior member and a lid body.

As shown in FIG. 9A, in the present embodiment, an operation section body 3Ba includes a second exterior body 20A and a lid body 21. The lid body 21 closes an opening (see symbol 20Am in FIG. 9B) of the second exterior body 20A.

Figure 9B:
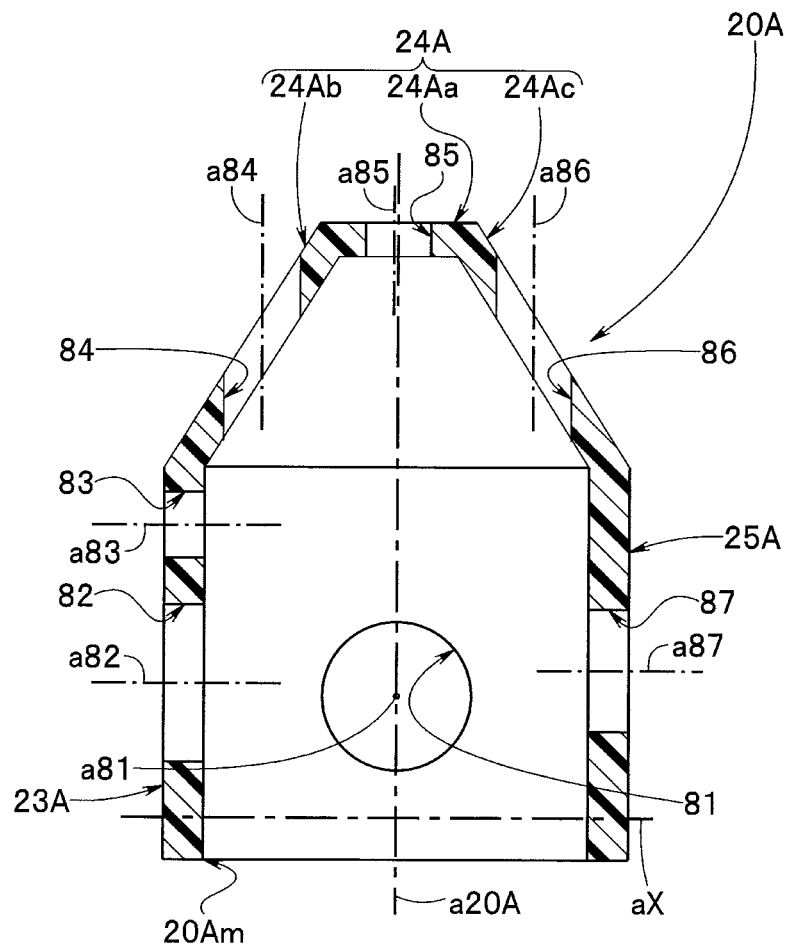
FIG. 9B is a diagram for illustrating a relationship between respective holes formed in the exterior member and a longitudinal direction axis and an orthogonal axis.

As shown in FIG. 9A and FIG. 9B, a plurality of through holes 81, 82, 83, 84, 85, 86, and 87 are formed in the second exterior body 20A.

The hole 81 for operation section support shaft having, for example, a circular cross-sectional shape is formed in one surface 22A of the second exterior body 20A. The hole 81 for operation section support shaft has a hole center axis a81 for support shaft which forms a first center axis. A frame shaft (not shown) of a bending operation portion 15 is disposed in the hole 81 for operation section support shaft.

In one side surface 23A of the second exterior body 20A, the hole 82 for suction button used both for air feeding and water feeding, and the hole 83 for push button switch each having, for example, a circular cross-sectional shape are formed. The holes 82 and 83 are formed as operating member arranging holes.

The hole 82 for suction button used both for air feeding and water feeding has a multi-use hole center axis a82 which forms the first center axis. The hole 83 for push button switch has a button switch hole center axis a83 which forms the first center axis.

One end surface 24A disposed adjacently to both one surface 22A and one side surface 23A has a ceiling surface 24Aa, one slanted surface 24Ab, and the other slanted surface 24Ac. The hole 84 for connecting first electric switch is formed in the one slanted surface 24b of the one end surface 24A, a hole 85 for electric switch is formed in the ceiling surface 24Aa, and a hole 86 for connecting second electric switch is formed in the other slanted surface 24Ac.

The hole 84 for connecting first electric switch, the hole 85 for electric switch, the hole 86 for connecting second electric switch are operating member arranging holes each having, for example, a circular cross-sectional shape.

The hole 84 for connecting first electric switch has a first switch connecting hole center axis a84 which forms the first center axis. The hole 85 for electric switch has an electric switch hole center axis a85 which forms the first center axis. The hole 86 for connecting second electric switch has a second switch connecting hole center axis a86 which forms the first center axis.

The hole 87 for cord having, for example, a circular cross-sectional shape is formed in the flat surface portion 25A. The hole 87 for cord has a cord hole center axis a87 which forms the first center axis. The universal cable 4 is made to pass through the hole 87 for cord.

An end portion of a first exterior body not shown is fixedly mounted in a watertight manner on an end surface of the second exterior body 20A disposed opposite to the ceiling surface 24a. The opening 20Am has, for example, a rectangular cross-sectional shape, and has an opening center axis which forms the first center axis.

In FIG. 9B, symbol a20A indicates a longitudinal direction axis of the second exterior body 20A and also is an opening center axis. In the present embodiment, the longitudinal direction axis a20A is orthogonal to the hole center axis a81 for support shaft of the hole 81 for operation section support shaft. Symbol aX indicates an orthogonal axis. The orthogonal axis aX is orthogonal to the longitudinal direction axis a20A.

The one side surface 23A and the other side surface 25A described above which are flat surfaces extending along the longitudinal direction axis a20A. The multi-use hole center axis a82, the button switch hole center axis a83, and the cord hole center axis a87 are arranged parallel to the orthogonal axis aX. The first switch connecting hole center axis a84, the electric switch hole center axis a85, the second switch connecting hole center axis a86, the opening center axis a20Am are arranged parallel to the longitudinal direction axis a20A.

Each of the multi-use hole center axis a82, the button switch hole center axis a83, the first switch connecting hole center axis a84, the electric switch hole center axis a85, and the first switch connecting hole center axis a86 is an arranging hole center axis.

Figure 10A:
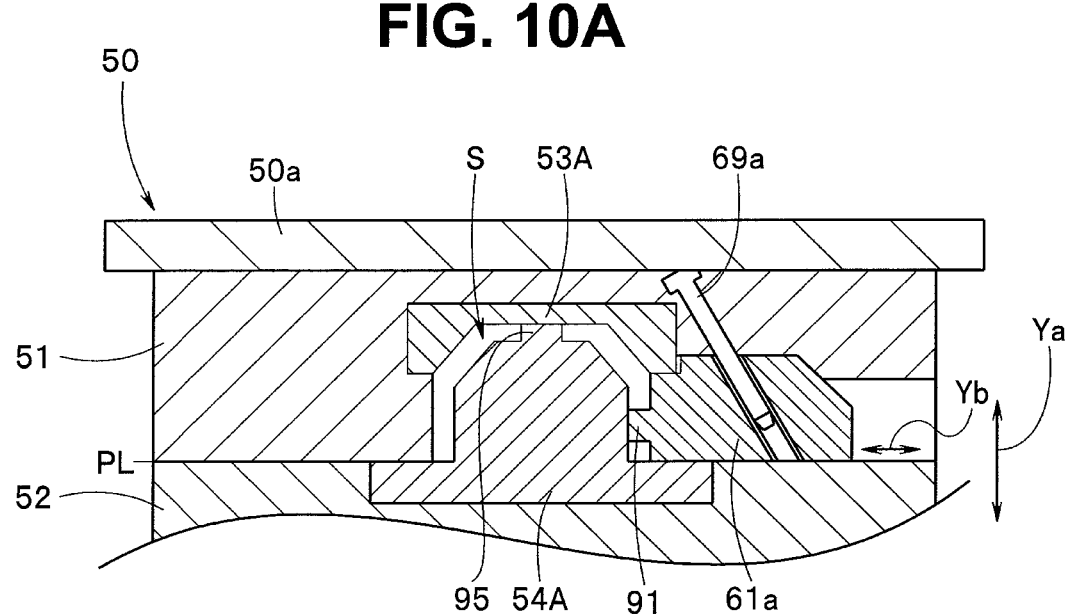
FIG. 10A is a diagram for illustrating a mold for forming a second exterior body of another configuration, and mainly illustrating a movable side block on which a protruding portion for forming a hole for electric switch is formed and a first slide core side where a protruding portion for forming a hole for operation section support shaft is formed.
Figure 10B:
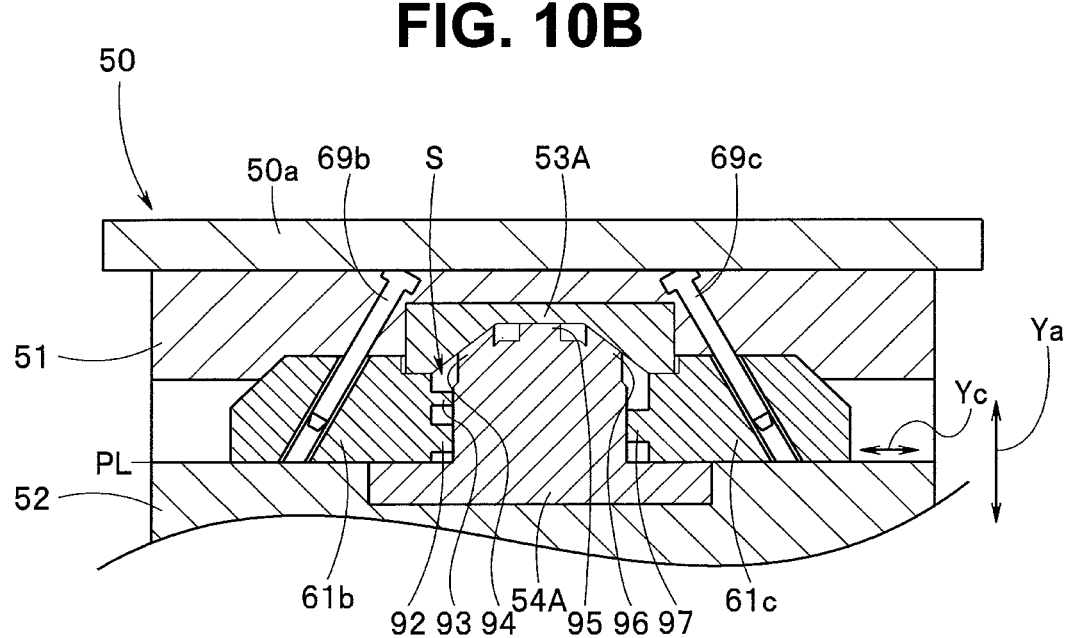
FIG. 10B is a diagram for illustrating the mold for forming the second exterior body by molding, and for illustrating a movable side block where a protruding portion for forming a hole for connecting an electric switch is formed in addition to the protruding portion for forming the hole for electric switch, a second slide core side where the second slide core side is movable in a first direction, and a protruding portion for forming a hole for suction button used both for air feeding and water feeding and a protruding portion for forming a hole for push button switch are formed, and a third slide core where the third slide core is movable in the first direction, and a protruding portion for forming a hole for cord is formed.
Figure 10C:
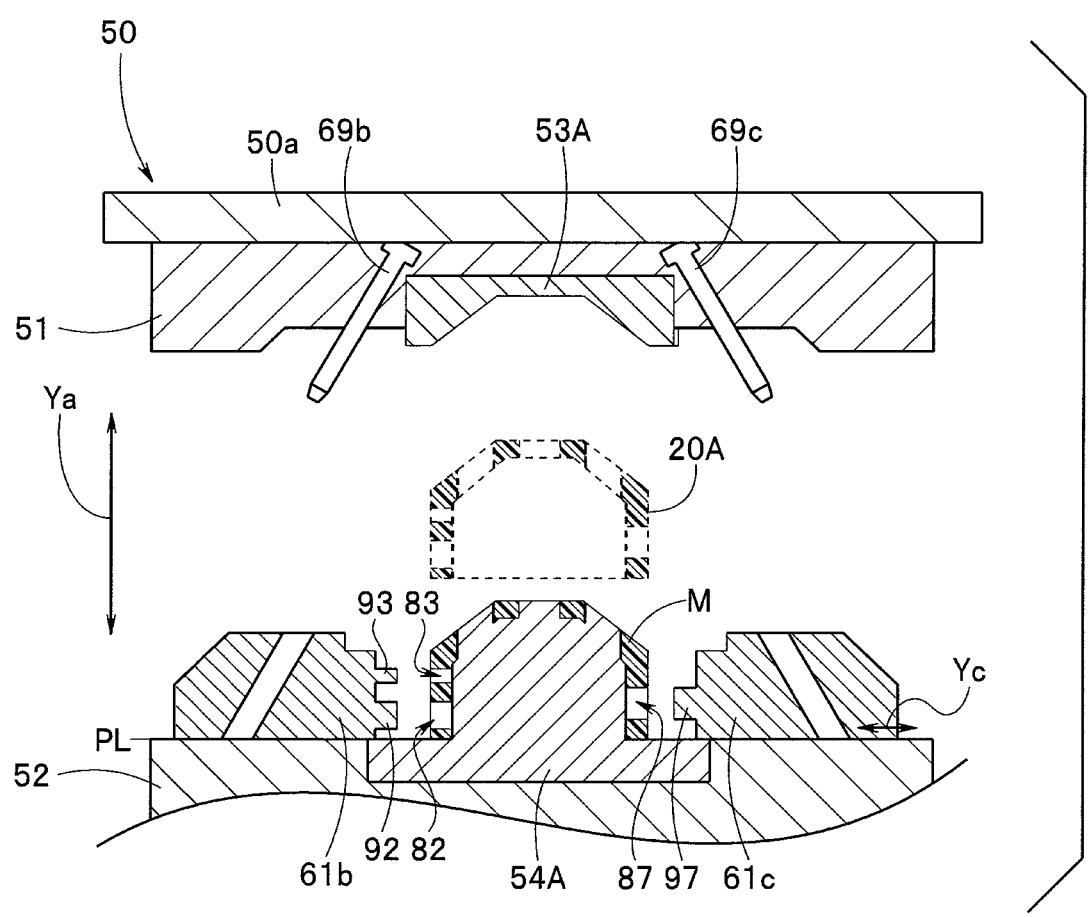
FIG. 10C is a diagram for illustrating the mold for forming the second exterior body by molding in an open state, and illustrating a molded product which remains in the movable block side and a second exterior body which is removed from the movable side block.

The second exterior body 20A described above is formed by resin molding using a mold 50 shown in FIG. 10A to FIG. 10C. Members identical with the corresponding members in the above-mentioned embodiment are described by giving same symbols and the description of the members is omitted.

As shown in FIG. 10A, FIG. 10B, and FIG. 10C, the mold 50 includes a fixed mold 51 and a movable mold 52. A fixed side block 53A which mainly forms an outer surface of the one end surface 24A of the second exterior body 20 is mounted on the fixed mold 51.

A movable side block 54A is mounted on the movable mold 52. A protruding portion 94 for first connection for forming the hole 84 for connecting first electric switch, a switch protruding portion 95 for forming the hole 85 for electric switch, and a protruding portion 96 for second connection for forming the hole 86 for connecting second electric switch are formed on the movable side block 54A.

Symbol 61a indicates a first slide core, symbol 61b indicates a second slide core, and symbol 61c indicates a third slide core.

A protruding portion 91 for forming the hole 81 for operation section support shaft is formed on the first slide core 61a. A protruding portion 92 for forming the hole 82 for suction button used both for air feeding and water feeding, and a protruding portion 93 for forming the hole 83 for push button switch are formed on the second slide core 61b. A protruding portion 97 for forming the hole 87 for cord is formed on the third slide core 61c.

In the present embodiment, when the movable mold 52 of the mold 50 moves in an opening direction of an arrow Ya so that the movable mold 52 changes from a closed state shown in FIG. 10A and FIG. 10B to an open state shown in FIG. 10C, the first slide core 61a moves in an outward direction of an arrow Yb by a first angular pin 69a. The second slide core 61b moves in an outward direction of an arrow Yc by a second angular pin 69b, and the third slide core 61c moves in the outward direction of the arrow Yc by a third angular pin 69c.

The direction of the arrow Ya which is an opening/closing direction of the mold in the present embodiment agrees with an extending direction of the longitudinal direction axis a20A of the second exterior body 20A formed by molding using the mold 50. The direction of the arrow Yb which is a moving direction of the first slide core 61a agrees with the hole center axis a81 for support shaft of the second exterior body 20A formed by molding using the mold 50. The direction of the arrow Yc which is a moving direction of the second slide core 61b and the third slide core 61c agrees with the orthogonal axis aX of the second exterior body 20A formed by molding using the mold 50.

An exterior body molding space (hereinafter, abbreviated as a sealed space) S which is formed in the mold 50 in a mold closed state shown in FIG. 10A and FIG. 10B is filled with molten resin. The resin filled in the sealed space S is cured by cooling.

After a predetermined time period elapses, the mold 50 is brought into an open state shown in FIG. 10C. In this case, the movable mold 52 moves in an opening direction of the arrow Ya in the drawing with respect to the fixed mold 51. As a result, the slide cores 61a, 61b, and 61c are moved along with the movement of the movable mold 52, and a cured molded product M remains in the movable side block 54A.

Then, an ejector pin not shown which is provided to the mold 50 is operated. As a result, the molded product M remaining on the movable side block 54A is removed from the movable side block 54A, and the second exterior body 20A indicated by a broken line is obtained.

Figure 11A:
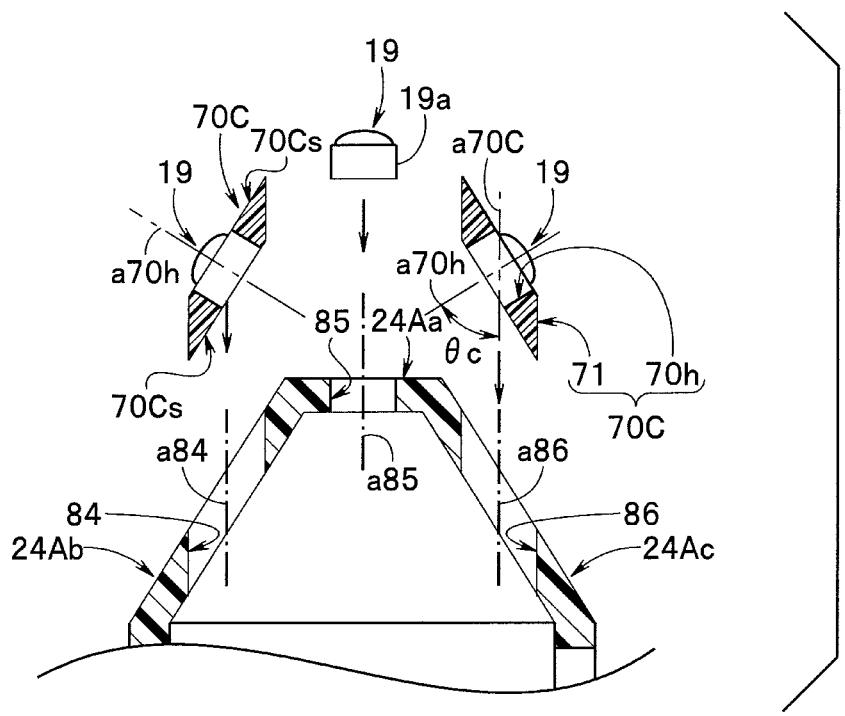
FIG. 11A is a diagram for illustrating a relationship between the electric switch and a switch fixing hole in a connecting member.
Figure 11B:
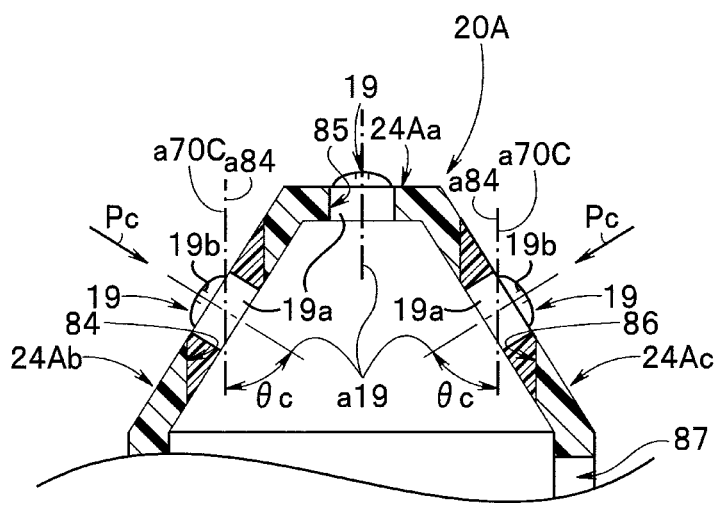
FIG. 11B is a diagram for illustrating an operation direction of the electric switch disposed on the connecting member which is fixedly mounted in a hole for electric switch, and an operation direction of a push button switch which is fixedly mounted in a hole for push button switch which is formed in a flat surface portion.

As shown in FIG. 11A and FIG. 11B, a switch body 19a of an electric switch 19 is accommodated and fixedly mounted in the hole 85 for electric switch.

In both the hole 84 for connecting first electric switch and the hole 86 for connecting second electric switch, an electric switch 19 is disposed together with a connecting member 70C.

The connecting member 70C has substantially the same configuration as the first connecting member 70A. The connecting member 70C has a switch fixing hole 70h and an outer peripheral surface portion 71. An outer diameter of the outer peripheral surface portion 71 is set such that the outer peripheral surface portion 71 is accommodated in the hole 84, 86 for connecting electric switch.

Symbol a70C indicates a member center axis. The member center axis a70C forms a second center axis, and is arranged parallel to the outer peripheral surface portion 71 of the connecting member 70C. The connecting member 70C is a circular columnar member having the outer peripheral surface portion 71. Both ends of the circular columnar member are formed into slanted surfaces 70Cs. One slanted surface 70Cs is substantially coplanar with an outer surface of the slanted surface 24Ab, 24Ac, and the other slanted surface 70Cs is substantially coplanar with an inner surface of the slanted surface 24Ab, 24Ac.

The switch fixing hole 70h is a through hole formed along a fixing hole center axis a70h in which the electric switch 19 is disposed. The fixing hole center axis a70h forms a third center axis.

In the present embodiment, the fixing hole center axis a70h of the switch fixing hole 70h is set orthogonal to the slanted surface 70Cs. Accordingly, the fixing hole center axis a70h intersects with the member center axis a70C of the connecting member 70 at an angle θc. The angle θc is an acute angle.

Before the connecting members 70C are respectively disposed in the holes 84, 86 for connecting electric switch, the electric switch 19 is disposed in the respective holes 70h for electric switch in a preliminarily set state as shown in FIG. 11A. The electric switch 19 is integrally and fixedly mounted in the respective holes 70h for electric switch in a watertight manner.

As shown in FIG. 11B, the connecting members 70C where the electric switch 19 is integrally fixedly mounted in each hole 70h for electric switch are disposed in the holes 84, 86 for connecting electric switch respectively. In such a configuration, the member center axis a70C of the connecting member 70C and the electric switch hole center axes a84, a86 are arranged parallel to each other or coaxially.

Then, the connecting members 70C are respectively fixedly mounted in the holes 84, 86 for connecting electric switch in a watertight manner. In such a configuration, the fixing hole center axis a70h is arranged in an intersecting manner with the electric switch hole center axes a84, a86 at a preliminarily set angle θc.

As a result, also in the second exterior body 20A of the present embodiment, when the moving member 19b of the electric switch 19 fixedly mounted in the switch fixing hole 70h is pushed in a direction of an arrow Pc intersecting with the switch connecting hole center axes a84, a86, the moving member 19b moves along the switch center axis a19. In other words, an operating direction of the electric switch 19 differs from the operating direction of the other switches, that is, the operating direction of the push button switch 18 and the operating direction of the electric switch 19.

In this manner, in mounting the electric switches 19 on the slanted surfaces 24Ab, 24Ac of the second exterior body 20A respectively, the holes 84, 86 for connecting electric switch each having the switch connecting hole center axes a84, a86 parallel to the longitudinal direction axis a20A are respectively formed in the slanted surfaces 24Ab, 24Ac.

The switch connecting hole center axes a84, a86 of the second exterior body 20A are made to agree with the opening/closing direction of the mold 50. With such a configuration, the hole 85 for electric switch and the holes 84, 86 for connecting electric switch can be formed in the second exterior body 20A in addition to the hole 81 for operation section support shaft, the hole 82 for suction button used both for air feeding and water feeding, the hole 83 for push button switch, and the hole 87 for cord without adopting a complicated mold structure.

In the present embodiment, a suction pipe sleeve for both air feeding and water feeding (not shown) is disposed and is fixedly mounted in the hole 82 for suction button used both for air feeding and water feeding in a watertight manner. An exterior portion of the push button switch 18 is disposed and is fixedly mounted in the hole 83 for push button switch in a watertight manner.

According to the present invention, it is possible to provide an endoscope which can, without adopting a complicated mold structure for forming exterior members, realize favorable user friendliness by mounting exterior members at optimum positions by taking into account operability of operating members.

The present invention is not limited to the above-mentioned embodiments, and various modifications are conceivable without departing from the gist of the present invention.

What is claimed is:

1. An endoscope comprising:
   a casing having a wall defining a hollow interior, the casing having a first through hole formed in the wall of the casing, the first through hole having a first center axis;
   an insert fixedly mounted in the first through hole; and
   a first operating member disposed in the insert, the first operating member having a first body fixed relative to the insert and a second body configured to move relative to the first body linearly along a second axis;
   wherein the insert is fixed in the first through hole such that the second axis is inclined relative to the first center axis of the first through hole.

2. The endoscope according to claim 1, wherein the insert includes:
   outer periphery fixed to an inner surface of the first through hole; and
   a fixing hole in which the first body of the operating member is fixedly mounted, the fixing hole having a second center axis parallel with the second axis.

3. The endoscope according to claim 2, wherein the second axis is coincident with the second center axis.

4. The endoscope according to claim 1, wherein:
   the insert fixedly mounted in the first through hole, the insert having a second through hole having a second center axis for accepting the first operating member, the second center axis being inclined relative to the first center axis.

5. The endoscope according to claim 4, wherein the casing further includes a third through hole having a third center axis, and
   the first center axis is inclined with respect to the third center axis.

6. The endoscope according to claim 5, wherein the second center axis is inclined relative to the third center axis.

7. The endoscope according to claim 1, wherein an outer periphery of the insert having a side surface inclined relative to the second axis.

8. The endoscope according to claim 7, wherein the side surface is parallel to the first center axis of the first through hole.

9. The endoscope according to claim 1, wherein an outer periphery of the insert has a circular cross-section.

10. The endoscope according to claim 1, wherein the casing is formed by resin molding.

11. The endoscope according to claim 1, wherein the casing forms an exterior of an operation portion of the endoscope.

12. The endoscope according to claim 1, wherein the first operating member is one of a mechanical button or an electrical switch.

13. The endoscope according to claim 1, further comprising:
   a second operating member disposed in the insert, and the second operating member having a third body fixed relative to the insert and a fourth body configured to move relative to the third body linearly along a third axis,
   wherein the third axis is inclined relative to the first center axis.

14. The endoscope according to claim 1, wherein
   the casing further includes a second through hole having a second center axis,
   the insert comprises a first insert,
   the endoscope further comprises:
      a second insert fixedly mounted in the second through hole; and
      a second operating member is disposed in the second insert, the second operating member having a third body fixed relative to the insert and a fourth body configured to move relative to the third body linearly along a third axis,
   wherein the second center axis is inclined relative to the third axis.

15. The endoscope according to claim 14, wherein
   the casing includes a first surface having the first through hole and a second surface having the second through hole, and
   the first surface is inclined relative to the second surface.

16. The endoscope according to claim 1, wherein the first through hole has a circular shape.

17. The endoscope according to claim 1, further comprising:
   an insertion portion provided distally relative to the casing; and
   an operation knob configured to operate the insertion portion,
   wherein the first operation member is provided farther away from the insertion portion than the operation knob.

18. The endoscope according to claim 17, wherein the operation knob rotates around a third axis,
   the second axis is inclined closer to the third axis than the first center axis.

19. An endoscope comprising:
   a casing having a wall defining a hollow interior, the casing having first and second surfaces, one of the first and second surfaces is offset at an angle greater than zero from the other of the first and second surfaces, the first and second surfaces having first and second through holes, respectively, the first and second through holes having first and second center axes, respectively, parallel to each other; and
   first and second moving members disposed in the first and second through holes, respectively, the first and second movable members being linearly movable along first and second axes, the first and second axes being inclined relative to each other.

20. A casing for an endoscope, the casing being for use with an operating member having a moving member configured to move linearly along a predetermined axis, the casing comprising:
   first and second surfaces, one of the first and second surfaces is offset at an angle greater than zero from the other of the first and second surfaces, the first and second surfaces having first and second through holes, respectively, the first and second through holes having first and second center axes, respectively, parallel to each other;
   at least one insert disposed in one of the first and second through holes, the at least one insert, having a third through hole for accommodating the operating member, the third through hole having a third center axis, and
   the third axis being inclined relative to the first and second center axes.

* * * * *